United States Patent [19]

Welch, Jr.

[11] Patent Number: 4,994,455

[45] Date of Patent: Feb. 19, 1991

[54] ANTI-ANXIETY AGENTS

[75] Inventor: Williard M. Welch, Jr., Mystic, Conn.

[73] Assignee: Pfizer Inc., New York, N.Y.

[21] Appl. No.: 477,835

[22] PCT Filed: Oct. 26, 1987

[86] PCT No.: PCT/US87/02855

§ 371 Date: Apr. 21, 1990

§ 102(e) Date: Apr. 21, 1990

[51] Int. Cl.$^5$ .................. C07D 401/14; C07D 403/14; C07D 405/14; A61K 31/505

[52] U.S. Cl. .................................... 514/216; 514/252; 514/253; 540/283; 544/230; 544/295; 544/296

[58] Field of Search ....................... 514/216, 252, 253; 540/583; 544/230, 295, 296

[56] References Cited

U.S. PATENT DOCUMENTS

| | | | |
|---|---|---|---|
| 4,605,655 | 8/1986 | Yevick et al. | 514/252 |
| 4,666,911 | 5/1987 | Fujimura et al. | 514/255 |
| 4,668,687 | 5/1987 | Yevich et al. | 514/252 |

Primary Examiner—John M. Ford
Attorney, Agent, or Firm—Peter C. Richardson; Paul H. Ginsburg; Karen De Benedictis

[57] ABSTRACT

Anti-anxiety agents; namely, 1-(heterocyclylcarbonyl)-3-[4-(2-pyrimidinyl)-1-piperazinyl]propanes and 1-(heterocyclylsulfonyl)-3-[4-(2-pyrimidinyl)-1-(piperazinyl)]propanes; and methods for their preparation and use.

13 Claims, No Drawings ced
ANTI-ANXIETY AGENTS

This application is entitled to the benefit of priority of PCT U.S. Pat. No. 87/02855, filed Oct. 26, 1987, as this application was filed under 35 USC 371 within 30 months, and a proper demand for International Preliminary Examination was made by the 19th month from that priority date.

BACKGROUND OF THE INVENTION

1. Field of the Invention

This invention relates to certain 1-acyl-3-[4-(2-pyrimidinyl)-1-piperazinyl]propanes useful as antianxiety agents. More specifically it relates to such compounds wherein the acyl substituent is a heterocyclyl carbonyl or a heterocyclyl sulfonyl group.

2. Prior Art

U.S. Pat. No. 3,717,634 describes a series of N-(heteroarcyclic) piperazinylalkyl-azaspiroalkanediones of the formula wherein A is $C_{2-6}$ alkylene; B is, inter alia, 2-pyrimidinyl; and n is 4 or 5. The compounds have tranquilizing and anti-emetic properties.

SUMMARY OF THE INVENTION

It has now been found that certain 1-acyl-3-[4(2-pyrimidinyl)-1-piperazinyl]propanes of formulae I and II are useful anti-anxiety agents. In the compounds of this invention the acyl substituents comprise certain heterocyclylcarbonyl groups (formula I), or certain heterocyclylsulfonyl groups (formula II). The general structure of formula (I) compounds is:

wherein R is

The general structure of formula (II) compounds is:

wherein $R^1$ is

Also included in this invention are pharmaceutically acceptable acid addition salts of compounds of formulae (I) and (II), pharmaceutically acceptable compositions comprising compounds of formula (I) or (II), or a salt of said compounds, and a pharmaceutically acceptable carrier, and the use of compounds of formulae (I) and (II) and/or their said salts for the treatment of anxiety in a mammal, especially a human, suffering therefrom.

The term pharmaceutically acceptable acid addition salts of the compounds of this invention of formulae (I) and (II) are the hydrochloride, hydrobromide, hydroiodide, sulfate, sulfamate, p-toluenesulfonate, acetate, lactate, citrate, tartrate, ascorbate, methanesulfonate salts and salts with other organic acids known to those skilled in the art and which find use in the preparation of pharmaceutically acceptable acid addition salts. Said salts are prepared by known procedures as, for example, by reacting the appropriate compound of formula (I) or (II) with one, or substantially one, equivalent of the desired acid in a reaction-inert solvent (ethanol, water, halogenated hydrocarbons) and recovering the salt by filtration or by evaporation of the solvent.

DETAILED DESCRIPTION OF THE INVENTION

The compounds of this invention having formula (I) are readily prepared by dehydrative coupling of 4-[4(2-pyrimidinyl)-1-pipirazinyl] butyric acid with the appropriate amine RH in a reaction-inert solvent; i.e., one which does not react with the reactants or products. Suitable dehydrating coupling agents are known to those skilled in the art and include carbodiimides such as dicyclohexylcarbodiimide and di-p-dimethylaminophenylcarbodiimide, N,N'-carbonyldiimidazole, n-ethyl-5-phenylisoxazolene-3'-sulfonate and diethylcyanophosphate. 1-hydroxybenzotriazole is generally added to the reaction mixture to facilitate coupling reaction. Representative reaction-inert solvents include methylene chloride, chloroform, tetrahydrofuran, dioxane and bis(2-methoxyethyl)ether.

While the stoichiometry of the coupling reaction requires equimolar amounts of the individual reactants, in practice the amine, acid, coupling agent and 1-hydroxybenzotriazole are generally used in a molar ratio of 1:1:1.1:1.5. Variations in the proportions of reactants used in order to optimize preparation of a given compound of formula (I) are, of course, within the skill of the art. The reaction is carried out at from about 0° C. to ambient temperature. The products are recovered by well known procedures.

The acid component, 4-[4-(2-pyrimidinyl)-1piperazinyl]butyric acid is usually available as its dihydrochloride salt and is therefore, used as such in the coupling reaction. For this reason, sufficient base is used in the reaction to neutralize the acid present in said salt. A variety of bases can be used. The preferred bases are tertiary organic amines such as triethylamine and N-methyl morpholine.

The 4-[4-(2-pyrimidinyl)-1-piperazinyl]butyric acid is prepared by reacting 1-(2-pyrimidinyl)-piperazine with ethyl 4-bromobutyrate in a reactioninert solvent, e.g. methyl isobutyl ketone, at the reflux temperature until reaction is essentially complete. Molar proportions of reactants are used along with a 10% excess of sodium bicarbonate as acid acceptor. Potassium iodide, from about 1% to 10% by weight of ethyl-4-bromobutyrate, is also used to expedite the reaction. The thus produced ester is isolated by filtration of solid by-products and removal of the solvent. Acid hydrolysis of the ester, e.g. with hydrochloric acid at the reflux temperature, affords the desired acid.

Formula (II) compounds are conveniently prepared by reaction of 1-(2-pyrimidyl)piperazine with an appropriate 3-chloropropylsulfonamide of the formula

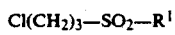

$Cl(CH_2)_3-SO_2-R^1$ wherein $R_1$ is as defined above. The reaction is carried out in a reaction-inert solvent, which can, in fact, be any solvent which does not enter into reaction with reactants or products. A preferred solvent is methyl isobutyl ketone. The reaction is carried out at the reflux temperature until complete or substantially complete. In general, reaction temperatures of about 60° C. to 150° C. are favored to facilitate the reaction. When the upper limit of the temperature range is selected for the reaction, a solvent such as bis(2-methoxymethyl) ether is selected.

The amine and chloropropylsulfonamide are generally reacted in a 1:1 molar ratio in the presence of an acid acceptor such as anhydrous carbonate, or a tertiary amine such as triethylamine, N-methylmorpholine or pyridine. To accelerate the reaction, potassium iodide is added to the reaction at from 1% to 10% by weight of chloro reactant. The product is recovered by known methods.

The required 3-chloropropylsulfonamides are readily prepared by reacting the appropriate amine $R^1H$ [wherein $R^1$ is a heterocyclyl moiety of formula (II-a-II-g) above] with 3-chloropropane sulfonyl chloride in methylene chloride at from about 0° to ambient temperature. In practice, one equivalent of the 3-chloropropanesulfonyl chloride is added to a solution containing one equivalent each of the appropriate amine and triethylamine at from about 0° C. to 10° C. When addition is complete, the reaction mixture is stirred an additional ten minutes and then warmed to room temperature. The product is isolated by extraction as illustrated herein.

The activity of the compounds of this invention as anti-anxiety agents is determined by a modification of the Vogel anti-conflict test. The procedure is based upon the ability of the test compounds to increase the number of shocks taken by thirsty rats that are shocked for drinking. The procedure comprises housing male CD rats (160-170g) on arrival at the test facility, 6 rats per cage, in the animal quarters for one week prior to experimentation. The animals are deprived of water for 48 hours before conflict testing.

Prior to testing, animals (N=8group) are placed into experimental chambers for a three minute training session. After location of the drinking spout, each animal is allowed three minutes of unpunished drinking, and is then removed from the chamber.

Animals are then injected with vehicle or drug, and after a variable pretreatment time, are placed back into the test chamber for the conflict test. After the first 20 licks a 0.5 second shock is presented via the drinking tube and the grid floor. Mouth shock, therefore, is controlled by the subject by withdrawal from the drinking tube. Thereafter, animals are shocked after every twentieth lick for a period of up to 15 minutes. Data from animals that do not find the drinking spout within the first five minutes are eliminated from the analysis. Data from the first 10 minutes after the first shock are analyzed.

A standard anxiolytic drug is administered and tested concurrently with screening compounds. The mean number of shocks taken by each group is statistically compared with the mean response of its appropriate control group.

The compounds of this invention at least double the number of shocks taken by the animals relative to the number taken by control groups; i.e., those receiving no anxiolytic agent.

When used for the treatment anxiety, they are used as is or in the form of pharmaceutical compositions comprising a formula (I) or (II) compound or a pharmaceutically acceptable acid addition salt thereof, and pharmaceutically-acceptable carriers or diluents. In a pharmaceutical composition comprising a compound of formula (I) or (II) or a pharmaceutically acceptable acid addition salt thereof, the weight ratio of carrier to active ingredient will generally be in the range of from 20:1 to 1:1, and preferably 10:1 to 1:1. However, in any given case, the ratio selected will depend on such factors as the solubility of the active ingredient, the dosage contemplated, and the precise dosage range. For oral administration, the preferred route for administering said compounds, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

When a compound of the present invention is to be used in a human subject, the daily dosage will be determined by the prescribing physician. In general, the dosage will depend on the age, weight and response of the individual patient, as well as the severity of the patient's symptoms. However, in most instances, an effective anxiety-alleviating amount of a compound of the formula (I) or (II), or a pharmaceutically-acceptable acid-addition salt thereof, will be from 1 to 300 mg per day, and preferably 5 to 100 mg per day, in single or divided doses. Naturally, the more active compounds of the invention will be used at the lower doses, while the less active compounds will be used at the higher doses.

The following examples and preparations are being provided solely for further illustration. For nuclear magnetic resonance spectra (NMR spectra), absorptions are given in parts per million (ppm) downfield from tetramethylsilane.

EXAMPLES 1–14

General Preparation of Formula (I) Compounds

A solution of the appropriate amine, one molar equivalent of 4-[4-(2-pyrimidinyl)-1-piperazinyl]butyric acid dihydrochloride, 2 equivalents of triethylamine and 1.5 equivalents of 1-hydroxybenzotrizole in methylene chloride was placed in a three neck round bottom flask fitted with a condenser, nitrogen atmosphere, magnetic stirrer and thermometer and was cooled to 0° C. in an ice/salt water bath. 1.1 equivalents of dicyclohexylcarbodiimide was then added. The resulting mixture was stirred at 0° C. for 3 hours, then allowed to warm to room temperature, and stirred overnight at room temperature.

Dicyclohexylurea (DCCU) was filtered off and the filtrate washed (3X) with 100ml water and twice with saturated sodium bicarbonate solution to remove traces of 1-hydroxybenzotriazole. The aqueous layers were combined and backwashed with methylene chloride. The combined organic layers were dried, filtered and evaporated to yield a semi-solid. The semi-solid was taken up in a minimal amount of acetone and stirred for one hour to crystallize any remaining traces of DCCU. The insoluble material was filtered and the filtrate was condensed to a brown oil.

Purified products were obtained either from direct crystallization of the oil from ethyl acetate or by flash column chromatography on silica gel. Final products were then recrystallized from ethyl acetate. Yields were not optimized.

The following compounds were thus prepared.

| EX. | R = group | M.P. °C. | % Yield | NMR (ppm) | IR (KBr) microns | HRMS (m/e) |
|---|---|---|---|---|---|---|
| 1 | a | 115–116 | 18 | (CDCl$_3$) delta 8.26 (2H,d) 7.20–7.40 (5H,m) 6.42 (1H,t) 3.80 (4H,t) 3.38 (2H,t) 3.10 (2H,t) 2.30–2.50 (12H,m) 1.92-(3H,s) 1.80–1.90 (2H,m) | 2.96, 3.44, 3.56, 6.00, 6.20, 6.44, 6.52, 6.78, 7.22, 7.42, 7.70, 8.00 | 435.2610 (M$^+$, calc'd. for C$_{25}$H$_{33}$N$_5$O$_2$: 435.2631), 435, 420, 272 (100%), 191, 177, 163 |
| 2 | b | 87–88 | 47 | (CDCl$_3$) 8.28 (2H,d) 6.42 (1H,t) 3.80 (4H,t) 3.54 (2H,t) 3.38 (2H,t) 2.48 (6H,t) 2.30–2.50 (4H,m) 1.96 (2H,t) 1.30–1.40 (2H,m) 0.98 (6H,s) | 3.45, 3.58, 3.65, 5.80, 6.18, 6.35, 6.45, 6.72, 6.98, 7.22, 7.42, 7.70, 8.00 | 345.2553 (M$^+$, calc'd. for C$_{19}$H$_{31}$N$_5$O: 345.2524), 345, 250, 225, 191, 182 (100%), 177, 163 |
| 3 | c | 98–99 | 22 | (CDCl$_3$) 8.30 (2H,d) 6.50 (1H,t) 3.80–4.00 | 2.92, 3.40, 3.50, 3.54, 6.14, 6.34, 6.52, 6.72, 6.94, 7.35, 7.86, 7.96 | 371.2720 (M$^+$, calc'd. for C$_{21}$H$_{33}$N$_5$O: 371.2680), 371, 224, 208 (100%), |

-continued

| EX. | R = group | M.P. °C. | % Yield | NMR (ppm) | IR (KBr) microns | HRMS (m/e) |
|---|---|---|---|---|---|---|
| | | | | (4H, broad t) 3.54 (2H,t) 3.40 (2H,t) 2.40–2.70 (12H,m) 1.94 (2H,m) 1.54–1.70 (4H,m) 1.40–1.52 (4H,m) | | 191, 177, 163 |
| 4 | d | 138–139 | 20 | (CDCl$_3$) 8.30 (4H,m) 6.52 (1H,t) 6.48 (1H,t) 3.80–3.90 (8H,m) 3.70 (2H,t) 3.58 (2H,t) 2.40–2.60 (8H,m) 1.90–2.00 (2H,m) | 2.86, 3.42, 3.50, 3.58, 6.10, 6.34, 6.44, 6.72, 6.90, 7.40, 7.68, 8.00 | 396.2397 (M$^+$, calc'd. for C$_{20}$H$_{28}$N$_8$O: 396.2386), 396, 288, 233, 191, 177 (100%), 163 |
| 5 | e | 178–180 | 25 | (DMSO) 8.44 (2H,d) 6.78 (1H,t) 4.68 (2H,d) 3.00–3.60 (12H,m) 2.40 (2H,t) 1.70–2.02 (6H,m) | — | 303.1936 (M$^+$, calc'd. for C$_{16}$H$_{25}$N$_5$O: 303.2056), 303.3(P) 233, 208, 191, 177, 163, 148, 140 (100%) |
| 6 | f | 178–180 | 37 | (DMSO) 8.44 (2H,d) 6.80 (1H,t) 4.68 (2H,d) 3.38–3.60 (8H,m) 3.00–3.20 (4H,m) 2.44 (2H,t) 1.90–2.04 (2H,m) 1.40–1.64 (6H,m) | — | 317.2264 (M$^+$, calc'd. for C$_{17}$H$_{27}$N$_5$O: 317.2212), 317 (P) 222, 197, 191, 177, 163, 154 (100%) |
| 7 | g | 168–170 | 41 | (DMSO) 8.44 (2H,d) 6.80 (1H,t) 4.70 (2H,d) 3.40–3.60 (4H,m) 3.30 (2H,s) 3.18 (2H,s) 3.0–3.1 (4H,m) 2.38 (2H,t) 1.90–2.0 (2H,m) 0.90 (12H,s) | — | 359.2604 (M$^+$, calc'd. for C$_{20}$H$_{33}$N$_5$O: 359.2680), 360 (P) 239, 196 (100%), 191, 177, 163 |
| 8 | h | 114–115 | 34 | (CDCl$_3$) 8.30 (2H,d) 6.50 (1H,t) 3.82 (4H, broad t) 3.20–3.50 (4H,m) 2.10–2.60 (10H,m) 1.80–2.00 (2H,m) 1.30–1.70 (8H,m) | 3.40, 3.56, 3.68, 6.30, 6.52, 6.62, 6.90, 7.04, 7.28, 7.50, 8.02 | 357.2503 (M$^+$, calc'd. for C$_{20}$H$_{31}$N$_5$O: 357.2529), 357, 249, 194 (100%), 191, 177, 163 |
| 9 | i | 110–111 | 39 | (CDCl$_3$) 8.30 (2H,d) 6.42 (1H,t) 3.80 (4H, broad t) 3.60–3.70 (2H,m) 3.10–3.20 (2H,m) 2.00–2.60 (12H,m) 1.80–2.00 (2H,m) 1.30–1.50 (3H,m) 1.00–1.20 (3H,m) | 3.42, 3.54, 3.68, 6.18, 6.40, 6.52, 6.80, 7.02, 7.42, 7.70, 8.20 | 369.2556 (M$^+$, calc'd. for C$_{21}$H$_{31}$N$_5$O: 369.2529), 369, 274, 261, 249, 224, 2 (100%), 191, 177, 163 |
| 10 | j | 94–95 | 30 | (CDCl$_3$) 8.30 (2H,d) 6.44 (1H,t) 6.10–6.20 (2H,m) 3.82 (4H, broad t) 3.60–3.70 (2H,m) 3.20–3.40 (2H,m) 2.20–2.80 (12H,m) 1.80–2.00 (2H,m) 1.40–1.50 (2H,m) | 3.46, 3.58, 6.22, 6.38, 6.42, 6.82, 7.00, 7.40, 7.70, 8.20 | 367.2350 (M$^+$, calc'd. C$_{21}$H$_{29}$N$_5$O: 367.0372), 367, 301, 247, 204 191, 177 (100%), 3 |
| 11 | k | 123–124 | 21 | (CDCl$_3$) 8.30 (2H,d) 6.42 (1H,t) 4.34 (2H, broad s) 3.80–3.90 (6H,m) | 3.42, 3.52, 6.15, 6.38, 6.44, 6.70, 6.90, 7.30, 7.52, 7.92 | 371.231 (M$^+$, calc'd. for C$_{20}$H$_{29}$N$_5$O$_2$: 371.2321), 371, 251, 208 (100%), 191, 177, 163 |

-continued

| EX. | R = group | M.P. °C. | % Yield | NMR (ppm) | IR (KBr) microns | HRMS (m/e) |
|---|---|---|---|---|---|---|
|  |  |  |  | 3.20–3.30 (2H,m) |  |  |
|  |  |  |  | 2.20–2.60 (10H,m) |  |  |
|  |  |  |  | 1.80–2.00 (2H,m) |  |  |
|  |  |  |  | 1.60–1.80 (2H,m) |  |  |
|  |  |  |  | 1.42 (2H,d) |  |  |
| 12 | l | 105–106 | 22 | (CDCl$_3$) | 3.24, 3.30, 3.42, | 357.249 (M$^+$, calc'd. |
|  |  |  |  | 8.24 (2H,d) | 3.55, 3.60, 6.12, | for C$_{20}$H$_{31}$N$_5$O: |
|  |  |  |  | 6.42 (1H,t) | 6.35, 6.45, 6.92, | 357.2514), 357, |
|  |  |  |  | 3.80 (4H,t) | 7.30, 7.60, 7.78, | (100%), 191, 177, |
|  |  |  |  | 3.70 (2H,t) | 7.88 | 163 |
|  |  |  |  | 3.50 (2H,t) |  |  |
|  |  |  |  | 2.40–2.60 (8H,m) |  |  |
|  |  |  |  | 2.00 (2H,m) |  |  |
|  |  |  |  | 1.80–1.94 (2H,m) |  |  |
|  |  |  |  | 1.50–1.70 (8H,m) |  |  |
| 13 | m | 210–211.5 | 45 | (DMSO) | 3.25, 3.50, 3.58, | 371.2710 (M$^+$, calc'd. |
|  |  |  |  | 8.44 (2H,d) | 4.12, 6.32, 6.60, | for C$_{21}$H$_{33}$N$_5$O: |
|  |  |  |  | 6.80 (1H,t) | 7.02, 7.22, 7.38, | 371.2685), 371, 251, |
|  |  |  |  | 4.70 (2H,d) | 7.62, 7.90, 8.22 | 208 (100%), 191, 7, |
|  |  |  |  | 4.00 (1H,d) |  | 163 |
|  |  |  |  | 3.60–3.80 (5H,m) |  |  |
|  |  |  |  | 3.00–3.12 (4H,m) |  |  |
|  |  |  |  | 2.30–2.60 (4H,m) |  |  |
|  |  |  |  | 1.90–2.10 (2H,m) |  |  |
|  |  |  |  | 1.20–1.60 (6H,m) |  |  |
|  |  |  |  | 1.00 (6H,s) |  |  |
| 14 | n | 77–78 | 17 | (CACl$_3$) | 3.52, 3.58, 3.12, | 343.2348 (M$^+$, calc'd. |
|  |  |  |  | 8.30 (2H,d) | 6.28, 6.52, 6.78, | for C$_{19}$H$_{29}$N$_5$O: |
|  |  |  |  | 6.42 (1H,t) | 7.20, 7.64, 7.88 | 343.2368), 343, |
|  |  |  |  | 4.30 (1H,d) |  | 248, 203, 191, |
|  |  |  |  | 3.80 |  | 180 (100%), 177, 163 |
|  |  |  |  | (4H, broad t) |  |  |
|  |  |  |  | 3.60 (1H,d) |  |  |
|  |  |  |  | 3.10 (1H,d) |  |  |
|  |  |  |  | 2.20–2.70 (11H,m) |  |  |
|  |  |  |  | 1.80–2.00 (2H,m) |  |  |
|  |  |  |  | 1.40–1.80 (6H,m) |  |  |

EXAMPLES 15–21

General Preparation of Formula (II) Compounds

The 1-(2-pyrimidyl) piperazine hydrochloride salt was dissolved in water and then the solution was made strongly basic (pH 12–14) with 10% NaOH. The 2-phase mixture (the product is a yellow oil) was extracted three times with methyl isobutyl ketone (MIBK).

In a single necked round bottom flask equipped with a magnetic stirring bar, Dean-Stark water collector, condenser and nitrogen bubbler was placed the combined MIBK layers containing the 1-(2-pyrimidinyl) piperazine free base. To this was added one equivalent of the corresponding appropriate 3-chloropropyl sulfonamide [Cl(CH$_2$)$_3$—SO$_2$NR$^1$, wherein R$^1$ is as defined above], 1.3 equivalent of anhydrous Na$_2$CO$_3$, and a catalytic quantity of KI. The reaction was then refluxed overnight at a moderate rate.

The inorganic solids in the cooled reaction mixture were filtered from the reaction and the filtrate was evaporated to an oil. In most cases, the crude oil was chromatographed on silica gel, eluting with ethyl acetate. Occasionally, the product crystallized from the crude oil when dissolved in ethyl acetate. In all cases, crystallization of purified product from ethyl acetate or isopropyl alcohol afforded a pure crystalline product.

| EX. | R$^1$ = group | M.P. °C. | % Yield | NMR (ppm) | IR (KBr) microns | HRMS (m/e) |
|---|---|---|---|---|---|---|
| 15 | a | 117–118 | 15.9 | (CDCl$_3$) | 2.82, 3.38, 3.52, | 381.2191 (M$^+$, calc'd. |
|  |  |  |  | 8.28 (2H,d) | 6.31, 6.51, 6.75, | C$_{18}$H$_{31}$N$_5$SO$_2$: |
|  |  |  |  | 6.46 (1H,t) | 6.91, 7.30, 7.60, | 381.2200), 381, 273, |
|  |  |  |  | 3.81 (4H, broad s) | 8.70 | 261, 205, 177, |
|  |  |  |  | 3.22 (4H,t) |  | 126 (100%) |
|  |  |  |  | 3.00 (2H,t) |  |  |
|  |  |  |  | 2.52 (6H, broad s) |  |  |
|  |  |  |  | 2.04 (2H, broad s) |  |  |
|  |  |  |  | 1.54 (2H, broad s) |  |  |
|  |  |  |  | 1.42 (4H,t) |  |  |
|  |  |  |  | 0.94 (6H,s) |  |  |
| 16 | b | 115–116.5 | 9.8 | (CDCl$_3$) | 2.90, 3.38, 3.51, | 407.2383 (M$^+$, calc'd. |
|  |  |  |  | 8.27 (2H,d) | 6.28, 6.50, 6.69, | C$_{20}$H$_{33}$N$_5$SO$_2$: |
|  |  |  |  | 6.45 (1H,t) | 6.78, 6.95, 7.42 | 407.2355), 407, 2 , |
|  |  |  |  | 3.80 (4H,t) |  | 287, 205, 177 (100%), |
|  |  |  |  | 3.24 (4H,t) |  | 162, 152, 108 |
|  |  |  |  | 2.98 (2H,t) |  |  |
|  |  |  |  | 2.43 (6H,m) |  |  |
|  |  |  |  | 2.0 (2H,m) |  |  |

-continued

| EX. | $R^1$ = group | M.P. °C. | % Yield | NMR (ppm) | IR (KBr) microns | HRMS (m/e) |
|---|---|---|---|---|---|---|
| 17 | c | 152–153.5 | 27.8 | 1.32–1.64 (12H,m) (CDCl$_3$) 8.30 (2H,d) 7.41 (2H,d) 7.32 (2H,d) 6.50 (1H,t) 3.72–3.90 (6H,m) 3.28 (2H,t) 3.09 (2H,t) 2.54–2.64 (6H, broad s) 2.10–2.21 (4H,m) 1.80–1.84 (2H,m) | 3.20, 3.38, 3.44, 3.55, 6.30, 6.45, 6.70, 6.85 | 479.1715 (M$^+$, calc'd. for C$_{22}$H$_{30}$N$_5$O$_3$SCl: 479.1756), 481, 479, 373, 371, 361, 35 177 (100%), 162, 148, 108 |
| 18 | d | 242–242.5 | 66.2 | (CDCl$_3$) 8.79 (1H, broad s) 8.50 (2H, d) 7.18–7.71 (7H,m) 7.08 (2H,d) 6.48 (1H,t) 4.50 (1H,m) 3.82–4.06 (6H,m) 3.12 (2H,t) 2.98 (2H,t) 2.46–2.64 (6H,m) 2.12 (2H,m) 1.92 (2H,m) 1.62 (2H,m) | 3.55, 5.90, 6.39, 6.45, 6.75, 6.90 | 485.2239 (M$^+$, calc'd. for C$_{23}$H$_{31}$N$_7$O$_3$S: 485.2209), 485, 365, 265, 177 (100%), 148 |
| 19 | e | 175.5–178 | 10.7 | 8.28 (4H,m) 6.50 (1H,t) 6.42 (1H,t) 3.92 (4H,t) 3.78 (4H, broad s) 3.30 (4H,t) 2.99 (2H,t) 2.40–2.50 (6H, broad s) 1.94–2.06 (2H,m) | 2.85, 3.32, 3.42, 3.48, 3.52, 3.58, 6.25, 6.40, 6.75, 6.96 | 432.2013 (M$^+$, calc'd. for C$_{19}$H$_{28}$N$_8$O$_2$S: 432.2056), 432, 337, 324, 298, 177 (100%) 148, 122, 108 |
| 20 | f (endo form) | 135.5–137 | 15.2 | (CDCl$_3$) 8.14 (2H,d) 6.34 (1H,t) 3.62–3.80 (4H, broad s) 3.24–3.40 (2H,d) 2.89–3.10 (4H,m) 2.34–2.56 (6H,m) 2.12–2.22 (2H, broad s) 1.90–2.06 (2H, broad s) 1.22–1.62 (8H,m) | 1.91, 3.38, 3.48, 3.52, 3.54, 3.60, 6.35, 6.52, 6.80, 6.92, 7.39, 7.52, 7.68, 7.80, 7.91 | 405.2216 (M$^+$, calc'd. for C$_{20}$H$_{31}$N$_5$O$_2$S: 405.2198), 405, 297, 285, 205, 177 (100%), 162, 151, 148 |
| 21 | g (endo form) | 223–224 (HCl salt) | 5.7 | (DMSO) 8.42 (2H,d) 6.74 (1H,t) 6.24 (2H,s) 4.62–4.74 (2H,d) 2.76–3.59 (16H,m) 2.00–2.17 (2H, broad s) 1.40–1.49 (2H, broad s) | 2.89, 3.40, 3.49, 3.90, 4.09, 6.28, 6.45, 6.70, 6.85, 6.98, 7.18, 7.26, 7.50, 7.89 | 403.2061 (M$^+$, calc'd. for C$_{20}$H$_{29}$N$_5$O$_2$S: 403.2042), 403, 295, 283, 265, 177 (100%), 1.62, 1.48, 136, 2, 111, 108 |

PREPARATION 1

Ethyl-4-[4-(2-pyrimidinyl)-1-piperazinyl]butyrate 1.2 equivalents of 1-(2-pyrimidinyl)piperazine hydrochloride was dissolved in water and the solution made strongly basic (pH 12–14) with 10% NaOH. The 2-phase mixture (the product is a yellow oil) was extracted three times with methyl isobutyl ketone (MIBK). The MIBK solution resulting was placed in a single neck round bottom flask fitted with magnetic stirrer, condenser and nitrogen atmosphere, and a Dean-Stark trap. To this solution was added 1 equivalent of ethyl 4-bromobutyrate, 1.1 equivalent of Na$_2$CO$_3$ and a catalytic quantity of KI. The resulting mixture was then refluxed for 4 hours and then cooled to room temperature. Inorganic solids were filtered off and the filtrate was condensed to give the title compound yellow oil. Yield 75%.

PREPARATION 2

4[4-(2-Pyrimidinyl)-1-piperazinyl]-butyric acid hydrochloride

The ester of Preparation 1 and 6N HCl were placed in a round bottom flask fitted with magnetic stirrer, nitrogen atmosphere, and a condenser and refluxed for 2 hours. The mixture was then cooled and the water stripped in vacuo to give the title acid (70% yield) as a pale yellow solid which was used without further purification. MP=254-255° C. M/e: 250, 191, 177, 163, 122, 108 (100%), 80.

NMR (DMSO), ppm: 8.44 (2H, d), 6.80 (1H, t), 4.62 (2H, d), 3.52 (2H, d), 3.38-3.50 (2H, broadened t), 3.00-3.20 (4H, m), 2.32 (2H, t), 1.70-2.0 (2H, m).

PREPARATION 3

General Method for 3-chloropropylsulfonamides:

Cl(CH$_2$)$_3$—SO$_2$—R$^1$.

A solution containing 1 equivalent of the appropriate amine R$^1$H (defined above) and 1 equivalent of triethylamine in methylene chloride was cooled to 0°-5° C. in an ice salt bath. After the mixture was cooled, 1 equivalent of 3-chloropropane sulfonyl chloride was added dropwise while maintaining the temperature between 0° and 10° C. The reaction mixture was then stirred in the ice bath an additional ten minutes and then warmed to room temperature.

The reaction mixture was poured into water. The organic layer was extracted three times with water and then the combined aqueous phases were combined and extracted twice with methylene chloride. The organic layers were combined, washed with brine, dried and evaporated to yield the crude (3-chloropropyl sulfonamide, Cl(CH$_2$)$_3$—SO$_2$—R$^1$) wherein R$^1$ is as defined herein, which can be used in examples 10-14 without further purification.

I claim:

1. A compound having the formula (I)

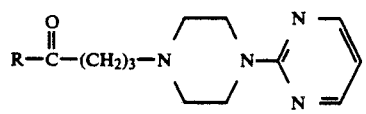

or a pharmaceutically acceptable acid addition salt thereof wherein R is group:

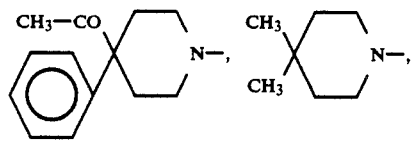

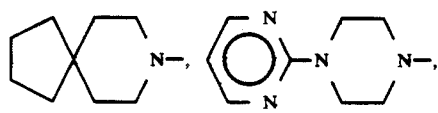

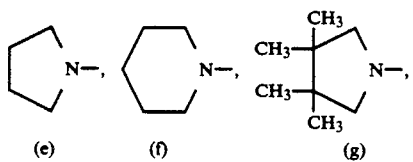

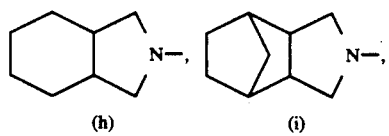

-continued

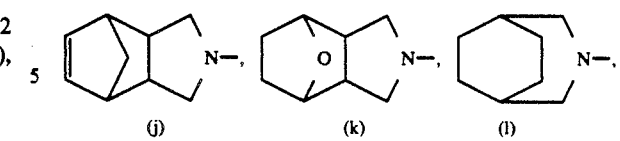

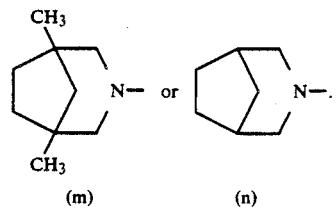

2. The compound according to claim 1 wherein R is group (C).

3. The compound according to claim 1 wherein R is group (h).

4. The compound according to claim 1 wherein R is group (k).

5. The compound according to claim 1 wherein R is group (l).

6. A method of treating anxiety in a human suffering therefrom which comprises administering to said human an anti-anxiety treating amount of a compound according to claim 1.

7. A pharmaceutical composition for treating anxiety in a human suffering therefrom which comprises an anti-anxiety treating amount of a compound according to claim 1 and a pharmaceutically acceptable carrier.

8. A compound having the formula (II)

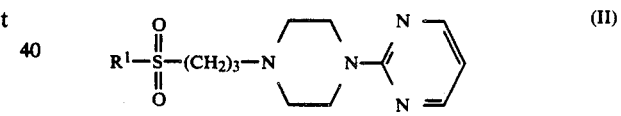

or a pharmaceutically acceptable acid addition salt thereof wherein R$^1$ is a group:

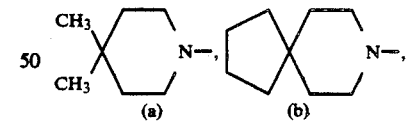

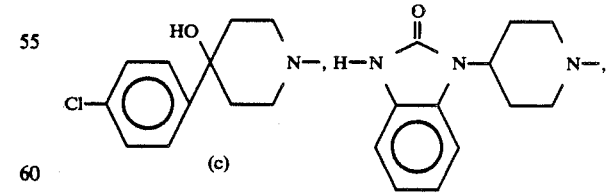

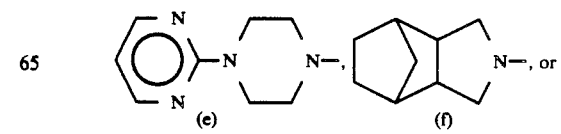

-continued

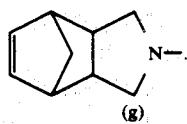
(g)

9. The compound according to claim 8 wherein R¹ is group (a).

10. The compound according to claim 8 wherein R¹ is group (e).

11. The compound according to claim 8 wherein R¹ is group (f).

12. A method of treating anxiety in a human suffering therefrom which comprises administering to said human an anti-anxiety treating amount of a compound according to claim 8.

13. A pharmaceutical composition for treating anxiety in a human suffering therefrom which comprises an anti-anxiety amount of a compound according to claim 8 and a pharmaceutically acceptable carrier.

* * * * *